United States Patent [19]
Derycke

[11] Patent Number: 5,776,195
[45] Date of Patent: Jul. 7, 1998

[54] PROCEDURE AND DEVICE FOR FACILITATING OSSEOUS GROWTH

[76] Inventor: Raymond René Derycke, 66, Avenue Victor Hugo, 75116 Paris, France

[21] Appl. No.: 773,085

[22] Filed: Dec. 24, 1996

[30]    Foreign Application Priority Data

Dec. 28, 1995 [FR]    France ............................ 95 15675

[51] Int. Cl.$^6$ ........................... A61F 2/28; A61C 13/12
[52] U.S. Cl. ..................... 623/16; 433/177; 433/178; 433/179; 433/201.1
[58] Field of Search ........................ 623/16; 433/177, 433/178, 179, 201.1

[56]    References Cited

U.S. PATENT DOCUMENTS

| | | | |
|---|---|---|---|
| 5,286,198 | 2/1994 | Barnes | 433/179 |
| 5,443,500 | 8/1995 | Sigwart | 623/1 |
| 5,545,226 | 8/1996 | Wingo et al. | 623/16 |
| 5,564,927 | 10/1996 | Barnes, Sr. et al. | 433/179 |

*Primary Examiner*—Paul P. Prebilic
*Attorney, Agent, or Firm*—Wenderoth, Lind & Ponack, L.L.P.

[57]    ABSTRACT

A procedure for facilitating osseous growth, particularly in dental surgery and in maxillofacial surgery, and device for implementing this procedure is disclosed. The device includes an elastic member which is interposed between bone surface and a membrane arranged beneath tissues overlying the bone surface. The elastic member is capable of lifting the membrane a slight distance with a controlled amount of pressure. In the procedure, the elastic member is held temporarily, until scarring has taken place, in a state in which the elastic device presents a minimum thickness between the osseous surface and the membrane and the elastic device does not exert any appreciable stress on the latter.

20 Claims, 2 Drawing Sheets

PROCEDURE AND DEVICE FOR FACILITATING OSSEOUS GROWTH

BACKGROUND OF THE INVENTION

The present invention relates to a procedure for promoting osseous growth, particularly in dental surgery or in maxillofacial surgery, and to a device allowing this procedure to be implemented.

It is often necessary, or desirable, after a traumatic or degenerative event, or else with a view to putting a prosthesis or an implant into place, to provoke osseous growth at the surface of a bone, such as, for example, a mandible, a maxilla, or a bone of the face.

The surgical technique used to this end consists in detaching a flap of periosteum from the osseous surface from which the osseous growth is intended to take place, and thereby the gain in thickness, so as to create, between the osseous surface and the overlying tissue, a space in which it will be possible for the osseous growth to take place.

To this end, having removed or separated the periosteum from the subjacent osseous surface, then having lifted all the overlying tissue from the bone, a non-permeable membrane is generally interposed between the freed osseous surface and the overlying flaps of tissue, beneath which membrane the osseous growth will occur. In order to create the space necessary for the osseous growth, the aim in to set this membrane at a distance from the subjacent osseous surface, which may, however, involve risks of infection or of fibrous necrosis and makes it more difficult or uncertain to ensure good closure and good scarring of the wound after the membrane has been put into place.

The volume subjacent to the membrane, in order to permit the osseous growth, is generally obtained by bone packing, which normally necessitates bone being taken from the patient, and this complicates and prolongs the intervention.

Under normal circumstances, given all these difficulties, an osseous gain of the order of 2 to 3 mm is considered a good result and a gain of the order of 5 mm is considered an exceptional result.

SUMMARY OF THE INVENTION

The present invention proposes overcoming these disadvantages and making available a procedure which makes it possible to improve osseous growth, to increase the gain in thickness, to dispense with the requirement for bone packing, and to reduce the risks of poor closure or scarring and the risks of fibrosis.

The invention therefore relates to a procedure for facilitating osseous growth, particularly in dental surgery or in maxillofacial surgery, in which procedure, after having removed the periosteum from the bone from which the growth in thickness is intended to take place, a membrane is interposed between the bone and the overlying tissues. The membrane is intended to delimit a volume at the surface of the bone, in which volume the osseous growth can take place after having verified the good closure and scarring of the overlying tissues, a stress or pressure of controlled intensity is applied to the membrane in order to create, between the bone and the membrane, a volume which is sufficient for good osseous growth.

Following the intervention, it in therefore possible to leave the overlying tissues to scar and obtain a good quality of these tissues, limiting the risks of necrosis, and then, once this result has been obtained, to form, between the tissue and the bone from which the periosteum has been removed, a volume permitting osseous growth.

The invention also relates to an implantable device for implementing this procedure, which includes an elastic means or member which is interposed between the bone and the membrane and which is capable of lifting the membrane a slight distance and with a pressure of controlled value, means are provided in order to hold the elastic member temporarily, until scarring has taken place, in a state in which the means presents a minimum overthickness between the osseous surface and the membrane and does not exert any appreciable stress on the latter.

In a particularly preferred embodiment, the means includes a spring of flat configuration and of very slight thickness, preferably made of a material with shape memory and designed to be interposed, thereby creating a alight overthickness, between the bone and the overlying tissue when it is in a retracted state also when stressed, means being provided to allow the spring to deform at the desired moment under the effect of its elasticity and to lift the membrane while stretching the overlying tissue, and to do this with a controlled stress.

The shape-memory material can advantageously be a metal material or alloy, and particular preference is given to nickel/titanium alloys comprising equal proportions.

The material can thus advantageously be chosen to remain in its neutral retracted position at a temperature below the natural temperature of the human body, for example at a temperature of the order of 20° C., and, when it in brought to a higher temperature, for example of the order of 35° C., to recover its elastic properties and to seek to relax, bearing on the osseous surface and exerting a tension on the overlying tissue.

However, the elastic member can also consist of, or incorporate, a spring, for example of metal, which does not possess shape memory.

The spring is preferably designed to exert on the membrane a pressure not exceeding 1.333 to 4.665 Pa (10 to 35 mmHg) and to move away from the bone on which it bears by a distance of the order of 5 to 15 mm.

Advantageously, the thickness of the spring, when stressed, is not greater than 1 to 3 mm.

In order to hold the spring in its flattened position, once it has been put in place and is heated to the temperature of the human body, a blocking means is advantageously provided, such as, for example, a suture which can be released from the outside by virtue of a suture thread exiting from the wound and capable of being acted on by the surgeon from the outside. It then suffices to pull on the suture in order to free it and to release the spring.

The spring can have any suitable shape, for example a zigzag shape normally held in one plane in the cold state, or else a helical shape, but also, of course, all shapes can be used which will permit the lifting of the membrane once the temporary holding means have been released and, if need be, the release temperature has been reached and the spring effectively released, with the desired pressure.

The spring can preferably consist of a wire folded in a zigzag and contained in one plane in the retracted state. When the temperature approaches the normal body temperature of 37°, higher than the transition temperature, the wire deform, bearing via its ends, and lifts the overlying metbrane, giving it a more or less spherical cupola shapes or else, in another embodiment, the shape of a portion of a cylinder.

In another embodiment, the spring wire can have a helical shape, for example square or circular.

The elastic member can also consist of an elastic web, continuous or openworked, or of a lattice, or of a plurality of associated springs, this structure being such that it tends to lift and curve inwards, at least in its central part, when the means temporarily holding it flat is relaxed.

The device according to the invention can also be made in the form of an elastic bellows or accordion structure which can move between a compressed position and an expanded position. This bellows structure can be formed, for example, by deformation of the central part of a metal sheet of small thickness, it being possible for the non-deformed periphery of the sheet to be shaped and cut out by the surgeon so as to adapt it to the tissue on which the device bears. In embodiments of this kind, the elastic bellows structure also serves as membrane, so that an associated membrane is no longer necessary.

The dimension of the device according to the invention in terms of length (X) and in terms of width (Y) is preferably of the order of 3 to 40 mm.

The dimension in terms of height (Z) is preferably of the order of 1 to 4 mm and very advantageously does not exceed 2 mm.

Taking into consideration the osseous surfaces normally concerned in dental or facial surgery, the force exerted by the spring can range, for example, from 5 to 200 g, and preferably from 30 to 100 g.

It is important to prevent the elastic member or spring from sliding along the osseous surface and moving away from the zone intended for the growth. To this end, it is preferable to secure the spring. For example, He spring can be secured against the subjacent bone via one or more parts of the spring which remain in the initial plane following deformation. This securing can be done, for example, by means of clips, screws or any other customary means. Alternatively, the spring can also be secured by suturing it to an element of overlying tissue in order to prevent it from moving in translation parallel to the osseous surface.

The ends of the spring, which are shaped so as to bear on the hard subjacent tissue, advantageously have loops, eyelets, or other configurations permitting their anchoring, for example by screws or clips to be secured in the osseous tissue.

The spring can also be secured beforehand to the membrane and thus be held in place by the membrane itself, the latter being optionally sutured to the overlying tissue. This securing to the membrane can be carried out in advance or else can be decided on by the surgeon on the spot.

For example, the spring, if it is made of wire, can be incorporated in a fine membrane, for example made of silicone.

BRIEF DESCRIPTION OF THE DRAWINGS

Other advantages and characteristic features of the invention will become clear from reading the following description which is given by way of non-limiting example and in which reference is made to the attached drawing, in which.

DETAILED DESCRIPTION OF THE INVENTION

Figures 1, 2:
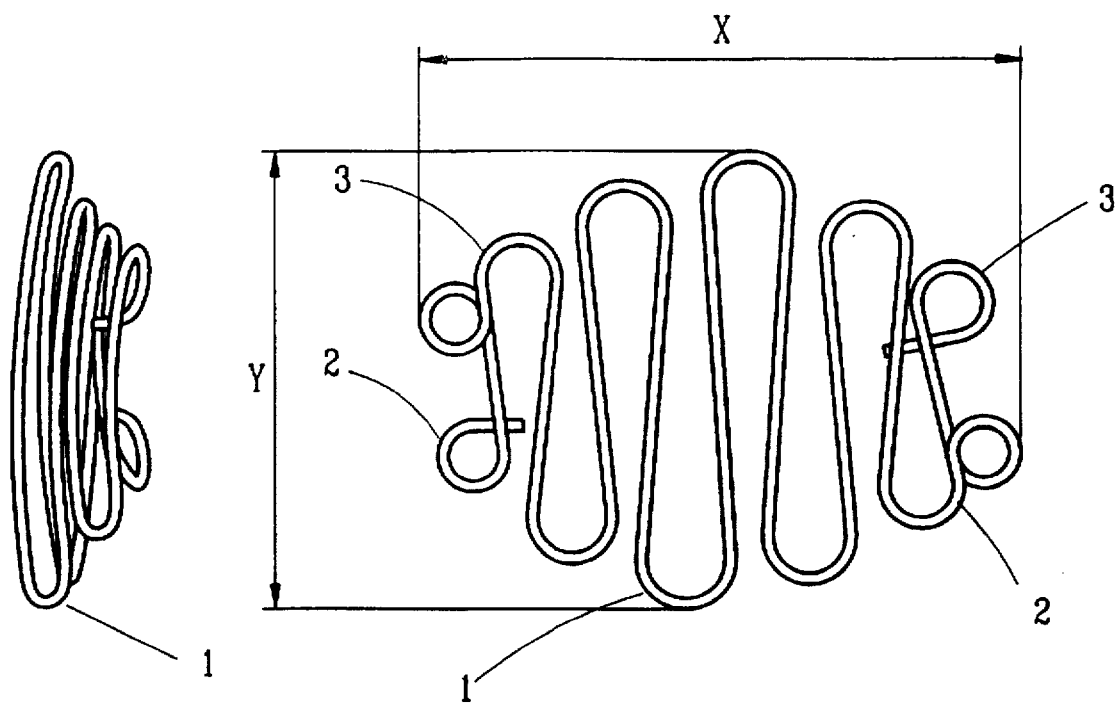
FIG. 1 represents a plan view of a spring according to the invention.
FIG. 2 represents an end view of the spring shown in FIG. 1.

The drawing represents an example of the device according to the invention in which an elastic member is a spring formed by a wire made of nickel/titanium alloy and having a diameter preferably equal to a value of between 0.43 and 0.83 mm. As can be clearly seen from FIG. 1, this spring, when viewed from above, has a zigzag configuration with maximum strand lengths in the central part, these diminishing progressively towards the two ends. The two ends of the wire 1 are curved to form two pairs of loops 2, 3. The length and width dimensions of this spring have been designated by X and Y.

Figures 3, 4:
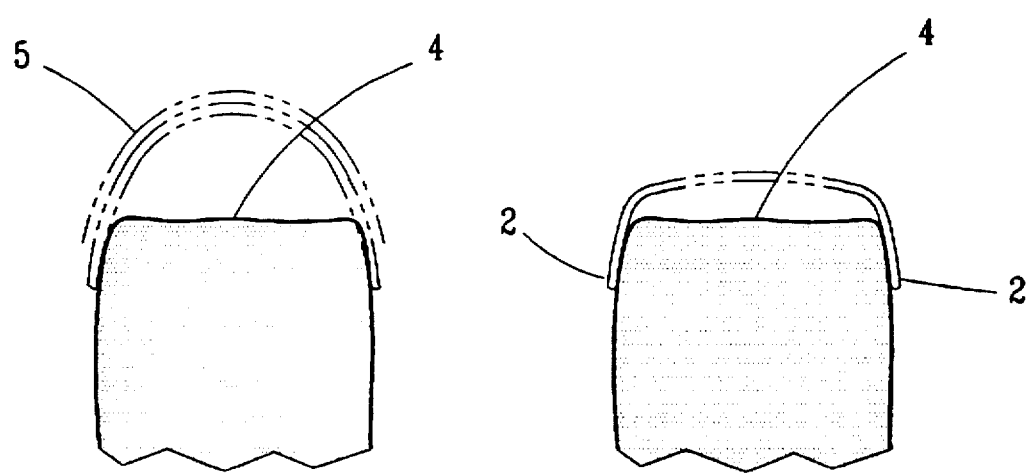
FIG. 3 represents a schematic profile view of the spring in a holding state.
FIG. 4 represents a schematic profile view of the spring in a released state.

This spring is seen in the holding state in FIG. 3. It presents a relatively flat profile, the ends in the area of the loops 2, 3, by contrast, are curved inwards to a greater extent, which allows it to be secured, for example by means of clips, against the two osseous faces which border osseous surface 4 which is to be raised, for example a maxilla. Moreover, as can be seen from FIG. 2, the various arms are also curved inwards in a plane perpendicular to the length X of the spring, that is to say in the direction Y, and it is preferred that the difference in level, in the height direction Z of the spring for one and the same strand of the zigzag spring, does not exceed approximately 2 mm.

In the illustrated example, the maximum dimensions X and Y are 20 and 16 mm, respectively, when the spring is retracted by a means holding it substantially flat, or else when it is cooled to a temperature below the release temperature defined by the choice of the alloy, for example 20° C. By contrast, when it is released, the same spring has dimensions X of 17.5 mm and Y of 15 mm.

When cold, or in the retracted state, that is to say in the state represented in FIG. 3, the dimension of the spring above the osseous surface 4 is of the order of 2 mm. When the spring is released, as can be seen in FIG. 4, the height of the spring above the bone is 7 mm and it thus lifts an overlying membrane 5 which has been interposed between the spring, when it was flat, and the overlying tissues.

The spring, made from this alloy with shape memory, presents, when cold, for example at the storage temperature of +4° C., the flattened appearance which is represented in FIG. 3. The surgeon, after freeing the osseous surface 4 and removing the periosteum, taken the cold spring and secures it quickly, via the loops 2, 3 formed at its two ends, against the osseous walls on each side of the osseous surface 4. In order to hold the spring in its flattened position, the surgeon immediately passes suture threads through the spring, for example in the direction X, this suture thread or these suture threads being fastened by a surgical knot which can be undone by pulling on the wire strand which will protrude from the wound. In this way, although the spring quickly reaches the temperature of 37.5°, it substantially retains its flattened shape. The surgeon places on the spring a membrane of conventional type which is intended to create the empty space for the osseous growth, and then returns the flaps of tissue and closes the overlying planes.

Once the wound has properly scarred, in general several weeks after the intervention, the surgeon pulls on the protruding part of the suture and releases the surgical knot. The spring relaxes immediately and then adopts the inwardly curved position represented in FIG. 4, in which position it lifts the membrane 5, creating between the membrane and the osseous surface an empty space having a height of the order of 5 to 7 mm.

Of course, the device according to the invention could also comprise its own temporary holding means, such as, for ale, filaments joining the loops 2 and 3 to one another over the length X of the spring, and which could have a strand which the surgeon would leave protruding from the wound in order to release the spring. An alternative, such holding means, filaments or others can be provided beforehand and will be released by the surgeon after he/she has fitted the suture thread or threads which will ensure that the spring according to the invention continues to be held in the flattened state.

Figure 5:
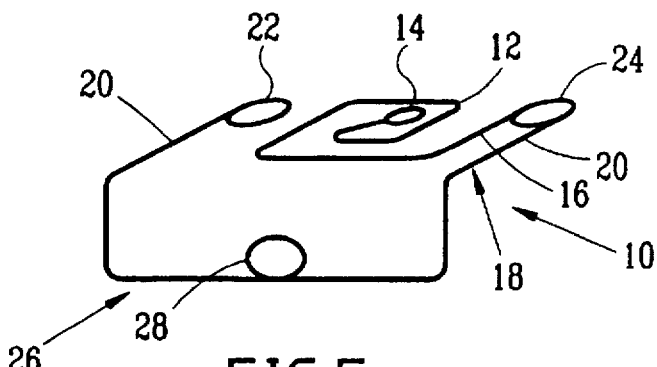
FIG. 5 is a perspective view of another illustrative embodiment of the device according to the invention.

FIG. 5 shows another illustrative embodiment of the device according to the invention. This example is distinguished essentially by the fact that the elastic member is a spring wire 10, of which the part forming the spring 12 has the shape of a square spiral. At its center, the spring 12 ends in a central securing loop 14 intended to hold the spring flat during the first phase of the surgical intervention. At its periphery, the spring 12 ends in a peripheral spiral turn 16 which extends via a part 18 serving as a base for supporting the spring 12 against the osseous surface. For this purpose, the supporting base 18 includes, on the one hand, a part 20 intended to be secured on the osseous surface by means of two securing loops 22 and 24 which are arranged on each side of the spring 12, and, on the other hand, a part 26 which is folded back at 90° and intended to be secured against an osseous face by means of a central loop 28.

To produce this device, use is made of the same metal that was used in the manufacture of the device in FIGS. 1 and 2. It is produced by shaping a single metal wire in which the loop 14 is first formed, after which the wire is wound to obtain the spiral forming the spring 12, and then the securing loop 24 is formed at the end of the peripheral spiral turn 16. The wire is then shaped so that it extends parallel to the osseous surface, two folds are made at 90°, the loop 28 in the area of the spring 12 is formed and two more folds are made at 90° in order to form the part 26. After the last fold, the metal wire is again parallel to the osseous surface, and the final securing loop 22 is formed.

Figure 6:
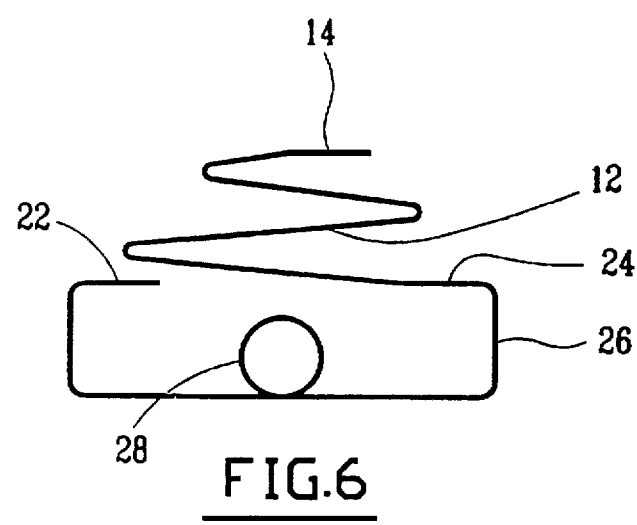
FIG. 6 represents a front view of the device shown in FIG. 5, in an opened out state.

The various phases of the surgical intervention are analogous to those described with regard to FIGS. 1 to 4. Once the wound has suitably scarred, the surgeon releases the spring 12 which assumes the general form of a truncated pyramid, so as to lift a membrane (not shown). In FIG. 6, the device is represented in a front view, with the spring part 12 in the opened-out state.

Of course, the spring can also have the form of a circular spiral.

It is advantageous for the device 10 to be incorporated in a fine membrane, for Ale made of silicone, so that a supplementary associated members is no longer necessary.

Figure 7:
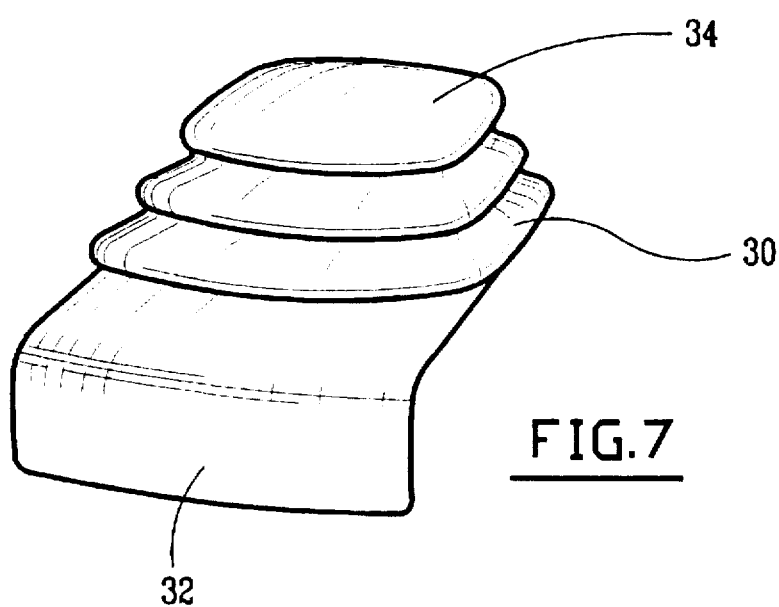
FIG. 7 is a perspective view of another alternative embodiment of the device according to the invention.

FIG. 7 shows yet another alternative embodiment of the device according to the invention. In this alternative embodiment, the device is made in the form of an elastic bellows structure 30 which is made entirely of metal. The same metal as was used to make the other alternative embodiments is advantageously used. The bellows structure 30 can be moved between a compressed, flattened position for the first phase of the surgical intervention, and an expanded position for the second phase in order to be able to lift the overlying tissue.

At its base, the bellows structure 30 is equipped with a skirt 32 intended to be cut and shaped by the surgeon in order to adapt it to the tissue on which the device bears.

Furthermore, at its top, the bellows structure 30 ends in a slightly bulged surface 34.

Advantageously, the bellows structure 30 also serves as membrane, so that a supplementary associated membrane is no longer necessary.

In a manner analogous to the other illustrative embodiments, the bellows structure 30 is held compressed during a first surgical phase, by holding means (not shown), and, after a period of scar formation, is released in order to lift the overlying tissues.

I claim:

1. An implantable device for facilitating osseous growth, said device comprising:

an elastic biasing structure for interposition between a surface of a bone and a membrane arranged beneath tissues overlying the bone, said elastic biasing structure being resiliently deformable between a retracted configuration and an expanded configuration, said elastic biasing structure at said retracted configuration presenting a minimum thickness which permits it to be interposed between the bone surface and the membrane, wherein said elastic biasing structure is capable of lifting the membrane with a controlled amount of pressure when said elastic biasing structure moves from said retracted position toward said expanded position; and holding means for temporarily holding said elastic biasing structure in said retracted configuration until scarring of the overlying tissues has taken place, wherein said elastic biasing structure, while in said retracted configuration, is capable of being interposed between the bone surface and the membrane without exerting any appreciable stress on the membrane, and when said elastic biasing structure moves from said retracted configuration to said expanded configuration, said elastic biasing structure is configured such that it can create an empty space over the bone surface.

2. The implantable device as claimed in claim 1, wherein said elastic biasing structure is made of a material with shape memory in order to exert a controlled pressure on the tissue.

3. The implantable as claimed in claim 2, wherein said shape-memory material is a nickel/titanium alloy of equal proportions.

4. The implantable device as claimed in claim 3, wherein said shape-memory material is a material which can remain in said retracted position at a temperature below that of the natural temperature of the human body.

5. The implantable device as claimed in claim 4, wherein said material is capable of remaining in said retracted position at a temperature of about 20° C.

6. The implantable device as claimed in claim 1, wherein said elastic biasing structure comprises a spring having a generally flat configuration and a very slight thickness in said retracted position, said spring being interposable between the bone and the overlying tissue when in said retracted configuration, and said spring being deformable at a desired moment due to its elasticity so as to be able to lift the membrane while stretching the overlying tissue, and to accomplish this with a controlled stress.

7. The implantable device as claimed in claim 1, wherein said elastic biasing structure comprises a wire spring folded in a zigzag shape, said wire spring lying in substantially one plane while in said retracted configuration.

8. The implantable device as claimed in claim 6, wherein said spring is formed of a wire folded in the form of a square or circular spiral which, in the retracted configuration, is held substantially in one plane.

9. The implantable device as claimed in claim 1, wherein said elastic biasing structure can exert on the membrane a pressure, which is less than or equal to 4.446 Pa, and can move the membrane by a distance of between 5 and 15 mm away from the bone surface on which said elastic biasing structure bears.

10. The implantable device as claimed in claim 1, wherein said elastic biasing structure has dimensions, in terms of length and in terms of width, in a range of between 3 and 40 mm.

11. The implantable device as claimed in claim 1, wherein the thickness of said elastic biasing structure, when in said retracted configuration, is not greater than 3 mm.

12. The implantable device as claimed in claim 11, wherein the thickness of said elastic biasing structure is less than or equal to 1 mm.

13. The implantable device as claimed in claim 1, wherein said holding means comprises a suture which can be released, when said device is implanted, from the outside by virtue of a suture thread exiting from the tissues.

14. The device as claimed in claim 1, wherein said elastic biasing structure includes, at both ends, a securing means for securing said elastic biasing structure on a subjacent tissue.

15. The implantable device as claimed in claim 14, wherein said securing means comprises a pair of wire loops.

16. The implantable device as claimed in claim 1, wherein said elastic biasing structure comprises an elastic bellows structure.

17. The implantable device as claimed in claim 1, wherein said elastic biasing structure is designed to exert on the membrane a pressure not exceeding 1.333 Pa and to move the membrane away from the bone on which said elastic biasing structure bears by a distance of between 5 and 15 mm.

18. A procedure for facilitating osseous growth, said procedure comprising:

removing periosteum from a surface of a bone at which osseous growth is intended;

interposing a membrane between the bone surface and tissues overlaying the bone, said membrane being intended to delimit a volume in which osseous growth, at the surface of the bone, can take place; and applying a stress or pressure of a controlled intensity to the membrane in order to create, between the bone and the membrane, a volume which is sufficient for good osseous growth, said stress or pressure being applied after having verified good closure and scarring of the overlying tissues.

19. The procedure as claimed in claim 18, wherein said procedure is for facilitating osseous growth in dental or maxillofacial surgery.

20. The procedure as claimed in claim 18, further comprising:

interposing a device between the bone surface and the membrane, said device including includes an elastic biasing structure which is resiliently movable between a retracted and an expanded position, wherein said device is inserted while said elastic biasing means is in the retracted position;

holding said interposed elastic biasing structure in the retracted position, wherein holding means are provided to hold said elastic biasing structure in said retracted position; and actuating said holding means to permit said elastic holding means to move from the retracted position in a direction toward the expanded position so as to effect said application of stress or pressure on the membrane.

* * * * *